US00PP21531P3

(12) United States Plant Patent
Carruth

(10) Patent No.: US PP21,531 P3
(45) Date of Patent: Nov. 30, 2010

(54) ***FLORIBUNDA* ROSE PLANT NAMED 'WEKGOJOLO'**

(50) Latin Name: *Rosa hybrida*
Varietal Denomination: WEKgojolo

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 188 days.

(21) Appl. No.: 12/287,475

(22) Filed: Oct. 9, 2008

(65) Prior Publication Data

US 2010/0095412 P1 Apr. 15, 2010

(51) Int. Cl.
*A01H 5/00* (2006.01)

(52) U.S. Cl. ..... Plt./145
(58) Field of Classification Search ..... Plt./145

See application file for complete search history.

(56) References Cited

U.S. PATENT DOCUMENTS

PP15,499 P2 * 1/2005 Olesen et al. ..... Plt./145
PP19,601 P2 * 12/2008 Kordes ..... Plt./145

* cited by examiner

*Primary Examiner*—Wendy C. Haas
(74) *Attorney, Agent, or Firm*—McKee, Voorhees & Sease, P.L.C.

(57) ABSTRACT

A new variety of *Floribunda* rose suitable for garden decoration, having flowers of neon yellow coloration.

1 Drawing Sheet

Classification: The present invention relates to a new *Rosa hybrida* plant.

Variety denomination: The new plant has the varietal denomination 'WEKgojolo'.

BACKGROUND OF THE INVENTION

This invention relates to a new and distinct variety of *Floribunda* Rose . It has as its seed parent the variety known as 'KORfalt' (not patented) and has an undisseminated seedling as its pollen parent with the following genetic origin 'WEKgibotex'×'SCRivluv'.

SUMMARY OF THE INVENTION

Among the features which distinguish the new variety from other presently available and commercial rose cultivars known to the inventor are the following combinations of characteristics: its unique and intense neon yellow flower coloration that last throughout the life of the flower, its pale yellow-green new foliage and its many stamens. The plant has a bushy upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKgojolo' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'KORfalt' by the following combination of characteristics: whereas 'WEKgojolo' bears double flowers (about 18 to 26 petals) of neon yellow coloration, 'KORfalt' bears double flowers of deep gold yellow coloration with significantly heavier petalage (about 25 to 30 petals). The new variety has a bushy upright medium height growing habit (about 90 to about 110 cm. in height); whereas the seed parent has a bushy rounded significantly shorter growing habit (about 50 to about 70 cm. in height).

The new variety may be distinguished from its pollen parent, an undisseminated seedling by the following combination of characteristics: whereas 'WEKgojolo' bears double (about 18 to 26 petals) medium sized flowers (about 5.7 to about 9.8 cm. in diameter), the undisseminated seedling bears semi-double (about 8 to 12 petals) flowers that are significantly smaller (about 3.2 to about 4.5 cm. in diameter). The new variety has a bushy upright medium height growing habit (about 90 to about 110 cm. in height); whereas the pollen parent has a bushy rounded significantly shorter growing habit.

COMPARISON WITH THE CLOSEST COMMERCIALLY AVAILABLE CULTIVAR

The closest commercially available cultivar to the new variety is the seed parent 'KORfalt'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of September. Phenotypic expression may vary with environmental, cultural and climatic conditions, as well as differences in conditions of light and soil.

Botanical designation: The new variety botanical designation is *Rosa hybrida* WEKgojolo.

FLOWER

The new variety sometimes bears its flowers singly, usually in clusters of three to five or more per stem. Flowers may be borne in regular rounded clusters on strong short to medium length stems (about 13 to about 38 cm.). Outdoors, the plant blooms abundantly and nearly continuously during the growing season. The flowers have a slight tea fragrance.

BUD

The peduncle is about 2.6 to about 5.5 cm. in length, of average caliper (about 0.2 to about 0.3 cm. in diameter), and usually erect. It is moderately smooth, with some stipitate glands and very few hairs. Peduncle color is between 146C and 144A.

Before the calyx breaks, the bud is about 1.0 to about 1.7 cm. in diameter at the widest point, about 1.6 to about 2.6 cm. in length, and pointed to somewhat ovoid in shape. The surface of the bud bears some foliaceous appendages and stipitate glands, usually with slender entire foliaceous parts extending beyond the tip of the bud about ½ or more of its length. Bud color is between 137C and 143A sometimes lightly suffused, especially on the side exposed to the sun, with between 183B and 187B.

The sepals are about 1.9 to about 3.6 cm. in length and about 0.6 to about 1.0 cm. in width at the widest point. The outer surface color of the sepal is between 137C and 143A sometimes lightly suffused, especially on the side exposed to the sun, with between 183B and 187B. The inner surface color of the sepal is near 138B broadly bordered by near 137B. After the sepals open, the inner surface color is sometimes lightly suffused, especially on the area exposed to the sun, with between 187A and 187B. The inner surface of the sepal is covered with fine wooly tomentum; sepal margins are lined with many stipitate glands and hairs.

The receptacle of the flower is of medium length (about 0.4 to about 0.6 cm.) and somewhat heavy in caliper (about 0.6 to about 0.7 cm. in diameter). The receptacle is cup-shaped in form. Its surface is very smooth with some hairs and with thick fleshy walls. The receptacle color is between 146C and 143A.

As the petals open (after the calyx breaks), the bud is about 1.4 to about 1.9 cm. in diameter at the widest point, about 2.1 to about 2.7 cm. in length, and pointed to somewhat ovoid in form. The color of the under surfaces of the newly opened petals is between 13B and 15C. There is no visible change in coloration at the point where the petal attaches. The color of the upper surfaces of the newly opened petals is between 12A and 15C. There is no visible change in coloration at the point where the petal attaches.

BLOOM

When fully open, the bloom ranges from about 5.7 to about 9.8 cm. in diameter. Petalage is double with about 18 to 26 petals and about 3 to 7 petaloids irregularly arranged. When partially open, the bloom form is moderately high centered to cupped, and the petals are somewhat tightly spiraled with petal edges slightly reflexed outward. When fully open, the bloom form is more cupped, and the petals are loosely cupped with petal edges moderately reflexed outward.

PETALS

The substance of the petals is moderately heavy and of somewhat thin thickness, with upper surfaces moderately satiny and under surfaces matte. The petals are about 2.2 to about 3.7 cm. in length and about 1.3 to about 3.2 cm. in width at the widest point. Petal margins are entire.

The outer petals are nearly round to somewhat obovate in shape with rounded apices.

The inner petals are moderately oblanceolate to somewhat obovate in shape with rounded apices.

Petaloids are about 0.7 to about 2.1 cm. in length and about 0.3 to about 1.3 cm. in width at the widest point. Petaloids are irregularly shaped somewhat oblanceolate to subulate with rounded apices.

NEWLY OPENED FLOWER

The under surface color of the outer, intermediate and inner petals is between 12B and 13B. There is no visible change in coloration at the point where the petal attaches. The upper surface color of the outer, intermediate and inner petals is between 8A and 12A. There is no visible change in coloration at the point where the petal attaches.

The under and upper surface color of the petaloids are similar in coloration to the upper and under surfaces of the intermediate and inner petals.

The general tonality of the newly opened flower is between 8A and 12A.

THREE-DAY-OLD FLOWERS

The under surface color of the outer, intermediate and inner petals is between 12C and 13C. There is no visible change in coloration at the point where the petal attaches. The upper surface color of the outer, intermediate and inner petals is between 8B and 12B. There is no visible change in coloration at the point where the petal attaches.

The under and upper surface color of the petaloids are similar in coloration to the upper and under surfaces of the intermediate and inner petals.

The general tonality of the three-day-old flower is between 8B and 12B.

On the spent bloom, the petals usually drop off cleanly.

In September in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 180) and are arranged regularly about the pistils; a few are mixed with petaloids. The filaments are of moderately short length (about 0.3 to about 0.8 cm.) most with anthers. Filaments are between 13A and 14B in color. The anthers are moderately small for the class and all open approximately at the same time. Anther color when immature is near 22A on the external part and near 10C on the internal part. Anther color at maturity is near 199D on the external part and near 200A on the internal part. Pollen is moderately sparse and near 13D in color.

FEMALE REPRODUCTIVE ORGANS

Pistils vary in number (average about 120). The styles are moderately even, average in length (about 0.4 to about 0.7 cm.), somewhat thin in caliper and loosely bunched. Stigma color is between 154C and 1C. Style color is between 154C and 145A sometimes lightly suffused with near 53D. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 6.5 to about 12.0 cm. in length and about 5.5 to about 10.8 cm. in width at the widest point, moderately heavy to somewhat crisp in texture, and glossy in finish on the upper side and matte in finish on the under side. The terminal leaflets are about 3.3 to about 7.0 cm. in length and about 2.1 to about 4.7 cm. in width at the widest point, shaped obovate with acute to somewhat acuminate apices and rounded bases. Their margins are usually simply serrate.

The upper surface color of the mature leaf is between 147A and 137A. The under surface color of the mature leaf is between 147B and 146B. The upper surface color of the young leaf is between 144A and 143A, sometimes lightly suffused mostly on the edge of the leaf with between 183B and 187B. The under surface color of the young leaf is between 146C and 143A, sometimes lightly suffused with between 183B and 187B.

The rachis is of average caliper and rough. The upper side is shallowly grooved with some hairs and stipitate glands on the edges of the grooves. The under side of the rachis is rough with some stipitate glands and small prickles. The rachis color is near 146B on the under side and near 137A on the upper side.

The stipules are about 1.0 to about 1.9 cm. in length and somewhat wide in width (about 0.4 to about 0.6 cm.) with medium length straight points that usually turn out at an angle of more than 45 degrees. The stipule color is between 137A and 137B.

The petiole is of average caliper and rough. The upper side is shallowly grooved with some hairs and stipitate glands on the edges of the grooves. The under side of the petiole is rough with some stipitate glands and small prickles. The petiole is about 0.5 to about 1.5 cm. in length and about 0.1 to about 0.2 cm in diameter at the widest point. The petiole color is near 146B on the under side and near 137A on the upper side.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has a bushy upright medium height growing habit (about 90 to about 110 cm. in height and about 50 to about 58 cm. spread at the widest point), with full branching. It displays vigorous growth and the canes are of somewhat heavy caliper for the class (about 1.2 to about 2.1 cm. in width at the widest point).

The color of the major stems is between 146A and 146B. They bear some large prickles that are about 0.7 to about 1.0 cm. in length. The large prickles are angled slightly downward with a moderately long narrow oval base; prickle color is between 166D and 165B. The major stem bears some small prickles of similar shape and coloration.

The color of the branches is between 146B and 137A. They bear few large prickles which are of similar shape to the large prickles on the major stems. Prickles are about 0.5 to about 0.7 cm. in length. Prickle color is between 146C and 152B sometimes lightly suffused with near 187D. The branches bear few small prickles of similar shape and coloration.

The color of the new shoots is between 146B and 143A sometimes lightly suffused with between 183C and 187C. They bear few large prickles which are of similar size and shape to the large prickles on the branches; prickle color is between 146C and 152B sometimes lightly suffused with near 187D. The shoots bear few small prickles of similar shape and coloration.

I claim:

1. A new and distinct *Floribunda* rose plant of the variety substantially as described and illustrated herein.

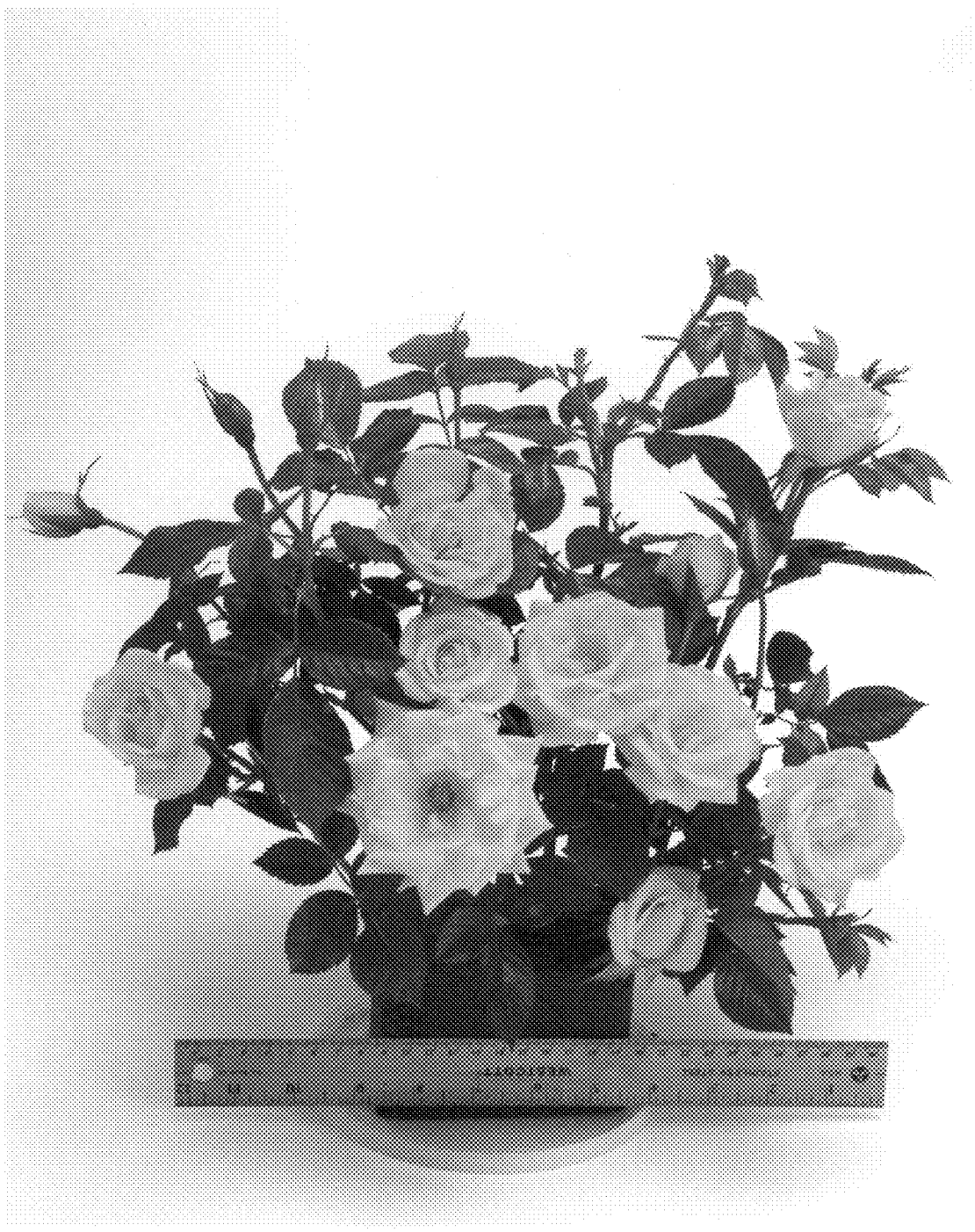

* * * * *